US009895342B2

(12) United States Patent
Maione et al.

(10) Patent No.: US 9,895,342 B2
(45) Date of Patent: Feb. 20, 2018

(54) CANNABINOIDS FOR USE IN THE TREATMENT OF NEUROPATHIC PAIN

(75) Inventors: Sabatino Maione, Naples (IT); Francesco Rossi, Naples (IT); Geoffrey Guy, Salisbury (GB); Colin Stott, Salisbury (GB); Tetsuro Kikuchi, Osaka (JP)

(73) Assignee: GW Pharma Limited, Cambridge (GB)

( * ) Notice: Subject to any disclaimer, the term of this patent is extended or adjusted under 35 U.S.C. 154(b) by 0 days.

(21) Appl. No.: 14/118,563

(22) PCT Filed: May 18, 2012

(86) PCT No.: PCT/GB2012/051129
§ 371 (c)(1),
(2), (4) Date: Nov. 19, 2013

(87) PCT Pub. No.: WO2012/160358
PCT Pub. Date: Nov. 29, 2012

(65) Prior Publication Data
US 2014/0107192 A1 Apr. 17, 2014
US 2014/0378539 A9 Dec. 25, 2014

(30) Foreign Application Priority Data
May 20, 2011 (GB) .................... 1108506.5

(51) Int. Cl.
*A61K 31/05* (2006.01)
*A61K 31/352* (2006.01)

(52) U.S. Cl.
CPC ............ *A61K 31/352* (2013.01); *A61K 31/05* (2013.01)

(58) Field of Classification Search
CPC .............................. A61K 31/05; A61K 31/352
USPC ......................... 514/454, 456, 733
See application file for complete search history.

(56) References Cited

U.S. PATENT DOCUMENTS

| 5,945,416 | A | 8/1999 | Womer |
| 6,730,330 | B2 | 5/2004 | Whittle et al. |
| 6,946,150 | B2 | 9/2005 | Whittle |
| 6,949,582 | B1 | 9/2005 | Wallace |
| 7,700,368 | B2 * | 4/2010 | Flockhart et al. ............ 436/177 |
| 7,709,536 | B2 | 5/2010 | Whittle |
| 7,968,594 | B2 | 6/2011 | Guy et al. |
| 8,053,476 | B2 | 11/2011 | Selve |
| 8,211,946 | B2 | 7/2012 | Whittle |
| 2003/0021752 | A1 | 1/2003 | Whittle et al. |
| 2004/0138293 | A1 | 7/2004 | Werner et al. |
| 2004/0192760 | A1* | 9/2004 | Whittle et al. ............ 514/454 |
| 2010/0016418 | A1 | 1/2010 | Guy et al. |
| 2010/0035978 | A1 | 2/2010 | Guy et al. |
| 2012/0245224 | A1 | 9/2012 | Guy et al. |

FOREIGN PATENT DOCUMENTS

| CA | 2 517 313 A1 | 2/2007 |
| GB | 2 377 633 A | 1/2003 |
| GB | 2 381 194 A | 4/2003 |
| GB | 2 391 865 A | 2/2004 |
| GB | 2 392 093 A | 2/2004 |
| GB | 2 394 894 A | 5/2004 |
| GB | 2 439 393 A | 12/2007 |
| GB | 2 448 535 A | 10/2008 |
| GB | 2 450 493 A | 12/2008 |
| WO | WO 02/064109 A2 | 8/2002 |
| WO | WO 02/069993 A1 | 9/2002 |
| WO | WO 03/037306 A2 | 5/2003 |
| WO | WO 2004/016246 A1 | 2/2004 |
| WO | WO 2005/120478 A1 | 12/2005 |
| WO | WO 2007/148094 A1 * | 12/2007 |

OTHER PUBLICATIONS

Examination Report for GB 0612512.4 dated Nov. 12, 2010.
Examination Report for GB 1108506.5 completed Sep. 13, 2011.
International Search Report and Written Opinion for International Application No. PCT/GB2006/004063, dated Jan. 2, 2007.
International Preliminary Report on Patentability for International Application No. PCT/GB2006/004063, dated Dec. 5, 2007.
International Search Report and Written Opinion for International Application No. PCT/GB2007/002315 dated Sep. 6, 2007.
International Preliminary Report on Patentability for International Application No. PCT/GB2007/002315 dated Jun. 19, 2008.
International Search Report and Written Opinion for International Application No. PCT/GB2012/051129 dated Aug. 14, 2012.
International Preliminary Report on Patentability for International Application No. PCT/GB2012/051129 dated Nov. 20, 2013.
[No Author Listed] "Cannabis-based medicines—high CBD, high THC, medicinal cannabis," Drugs in R&D 2003; 4(5):306-309.
Barnes, Sativex: clinical efficacy and tolerability in the treatment of symptoms of multiple sclerosis and neuropathic pain. Expert Opin Pharmacother. Apr. 2006;7(5):607-15.
Blake, et al., Preliminary assessment of the efficacy, tolerability and safety of a cannabis-based medicine (sativex) in the reatment of pain caused by rheumatoid artritis,Rheumatology 2006;45:50-52.
Colburn et al., Attenuated cold sensitivity in TRPM8 null mice. Neuron. May 3, 2007;54(3):379-86.
Costa et al., Oral anti-inflammatory activity of cannabidiol, a non-psychoactive constituent of cannabis, in acute carrageenan-induced inflammation in the rat paw. Naunyn Schmiedebergs Arch Pharmacol. Mar. 2004;369(3):294-9. Epub Feb. 12, 2004.
De Petrocellis et al., Plant-derived cannabinoids modulate the activity of transient receptor potential channels of ankyrin type-1 and melastatin type-8. J Pharmacol Exp Ther. Jun. 2008;325(3):1007-15. doi: 10.1124/jpet.107.134809. Epub Mar. 19, 2008.

(Continued)

*Primary Examiner* — Jennifer M Kim
(74) *Attorney, Agent, or Firm* — Wolf, Greenfield & Sacks, P.C.

(57) ABSTRACT

The present invention relates to cannabinoids for use in the treatment of neuropathic pain. Preferably the cannabinoids are one or more phytocannabinoids of: cannabigerol (CBG), cannabichromene (CBC), cannabidivarin (CBDV) or tetrahydrocannabivarin (THCV). More preferably the phytocannabinoids are isolated and/or purified from cannabis plant extracts.

9 Claims, 11 Drawing Sheets

(56) References Cited

OTHER PUBLICATIONS

Grond et al., Assessment and treatment of neuropathic cancer pain following WHO guildelines. Pain 79 (1999), pp. 15-20.
Hensen, B., "Cannabinoid therapeutics: high hopes for the future," Drug Discovery Today Apr. 1, 2005; 10(7):459-462.
Izzo et al., Non-psychotropic plant cannabinoids: new therapeutic opportunities from an ancient herb. Trends Pharmacol Sci. Oct. 2009;30(10):515-27.
Nurmikko, et al., A multi-centre, double-blind, randomized, placebo-controlled trial of oro-mucosal cannabis-based medicine in the treatment of neuropathic pain characterized by alloydnia. PO6. 119, Neurology, Mar. 2005, 64(6) Suppl. 1, p. A 374.
Perez, Combined cannabinoid therapy via an oromucosal spray. Drugs Today (Barc). Aug. 2006;42(8):495-503.
Perras, Sativex for the management of multiple sclerosis symptoms. Issues Emerg Health Technol. Sep. 2005;(72):1-4.
Polomano et al., A painful peripheral neuropathy in the rat produced by the chemotherapeutic drug, paclitaxel. Pain 94 (2001), pp. 293-304.
Puéchal et al., Peripheral neuropathy with necrotizing vasculitis in rheumatoid arthritis. A clinicopathologic and prognostic study of thirty-two patients. Arthritis Rheum. Nov. 1995;38(11):1618-29.
Russo et al., A tale of two cannabinoids: the therapeutic rationale for combining tetrahydrocannabinol and cannabidiol. Med Hypotheses. 2006;66(2):234-46. Epub Oct. 4, 2005.
Smith, GW-1000. GW Pharmaceuticals, Current Opinion on Investigational Drugs, Jul. 2004, 5(7), pp. 748-754.
The United Kingdom Parliament, Select Committee on Science and Technology Ninth Report (1998) at http://www.parliament.the-stationery-office.co.uk/pa/ld199798/ldselect/ldsctech/151/15101.htm.
The United Kingdom Parliament, Select Committee on Science and Technology Second Report (Mar. 14, 2001) at http://www.publications.parliament.uk/pa/ld200001/ldselect/ldsctech/50/5001.htm.
Third Party Observations for Application No. AU2012260611 mailed Dec. 20, 2014.
Third Party Observations for Application No. EP12722495.4 mailed Jan. 28, 2015.
Bakhsh et al., Miftaah-al-Khazaain. 1930: 607-8. Urdu. Exhibit 3.
Dasa et al., Bhaisajya Ratnavali. Chaukhamba Sanskrit Sansthan, Varanasi. Edn. 14. 2001: 347. Sanskrit. Exhibit 6.
Dasa et al., Brhat Nighantu Ratnakara (Saligramanighantubhusanam). vol. IV (Part VII).1997:170. Sanskrit. Exhibit 3.
Gupta et al., Bharata Bhaisajya Ratnakara. Jain Publishers, New Delhi, 2nd Edn. Aug. 1999:399. Sanskrit. Exhibit 5.
Guy et al., The development of Sativex® —A natural cannabis-based medicine Cannabinoids as Therapeutics. 2005: 231-63.
Khan et al., Khazaain-al-Adiva. vol. I. 1911: 886. Urdu. Exhibit 2.
Khan et al., Khazaain-al-Adiva. vol. I. 1911: 887. Urdu. Exhibit 5.
Khan et al., Khazaain-al-Adiva. vol. I. 1911: 889. Urdu. Exhibit 4.
Khan et al., Khazaain-al-Advia. vol. III. 1926: 519. Urdu. Exhibit 1.
Elsohly et al., Chemical constituents of marijuana: the complex mixture of natural cannabinoids. Life Sci. Dec. 22, 2005;78(5):539-48. Epub Sep. 30, 2005.
De Petrocellis et al., Effects of cannabinoids and cannabinoid-enriched Cannabis extracts on TRP channels and endocannabinoid metabolic enzymes. Br J Pharmacol. Aug. 2011;163(7):1479-94. doi: 10.1111/j.1476-5381.2010.01166.x.
Pertwee, The diverse CB1 and CB2 receptor pharmacology of three plant cannabinoids: delta9-tetrahydrocannabinol, cannabidiol and delta9-tetrahydrocannabivarin. Br J Pharmacol. Jan. 2008;153(2):199-215. Epub Sep. 10, 2007.
Wade et al., A preliminary controlled study to determine whether whole-plant cannabis extracts can improve intractable neurogenic symptoms. Clin Rehabil. Feb. 2003;17(1):21-9.

\* cited by examiner

Figure 1.

Different types of pain

Figure 2

Effects of treatment CBC (2.5 & 5 mg/kg, i.p.) on mechanical withdrawal threshold in SNI mice

Figure 3

Effects of treatment CBC (2.5 & 5 mg/kg, i.p.) on thermal withdrawal latency in SNI mice

Figure 4

Effects of treatment CBG (2.5 & 5 mg/kg, i.p.) on mechanical withdrawal threshold in SNI mice

Figure 5

Effects of treatment CBG (2.5 & 5 mg/kg, i.p.) on thermal withdrawal latency in SNI mice

Figure 6

Effects of treatment CBDV (2.5 & 5 mg/kg, i.p.) on mechanical withdrawal threshold in SNI mice

Figure 7

Effects of treatment CBDV (2.5 & 5 mg/kg, i.p.) on thermal withdrawal latency in SNI mice

Figure 8

Effects of treatment THCV (2.5 & 5 mg/kg, i.p.) on mechanical withdrawal threshold in SNI mice

Figure 9

Effects of treatment THCV (2.5 & 5 mg/kg, i.p.) on thermal withdrawal latency in SNI mice

Figure 10

Effects of treatment CBD (2.5 & 5 mg/kg, i.p.) on mechanical withdrawal threshold in SNI mice

Figure 11

Effects of treatment CBD (2.5 & 5 mg/kg, i.p.) on thermal withdrawal latency in SNI mice

CANNABINOIDS FOR USE IN THE TREATMENT OF NEUROPATHIC PAIN

RELATED APPLICATION

This application is a national stage filing under 35 U.S.C. § 371 of international application PCT/GB2012/051129, filed May 18, 2012, which was published under PCT Article 21(2) in English.

The present invention relates to cannabinoids for use in the treatment of neuropathic pain. Preferably the cannabinoids are one or more phytocannabinoids of: cannabigerol (CBG), cannabichromene (CBC), cannabidivarin (CBDV) or tetrahydrocannabivarin (THCV). More preferably the phytocannabinoids are isolated and/or purified from cannabis plant extracts.

BACKGROUND TO THE INVENTION

Figure 1:
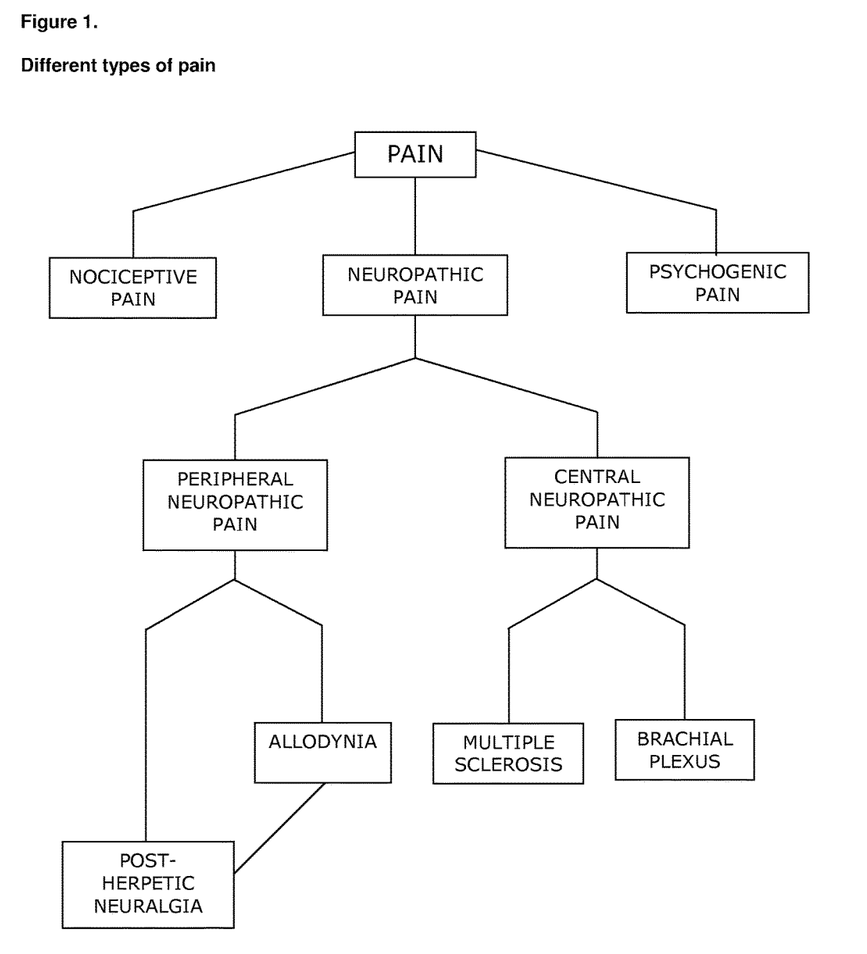
FIG. 1 shows the different types of pain that exist.
Figure 2:
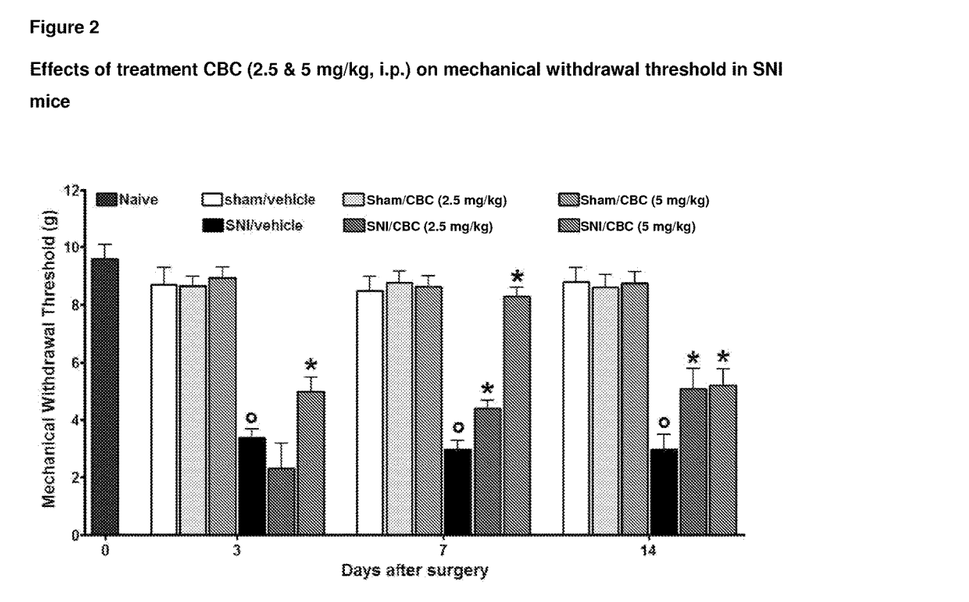
FIG. 2 shows the effects of treatment with CBC (2.5 & 5 mg/kg, i.p.) on mechanical withdrawal threshold in SNI mice.
Figure 3:
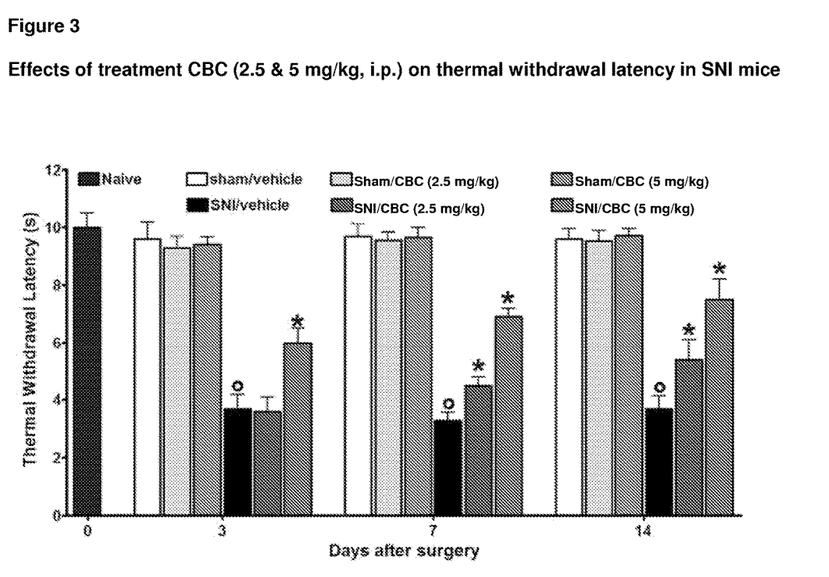
FIG. 3 shows the effects of treatment with CBC (2.5 & 5 mg/kg, i.p.) on thermal withdrawal latency in SNI mice.
Figure 4:
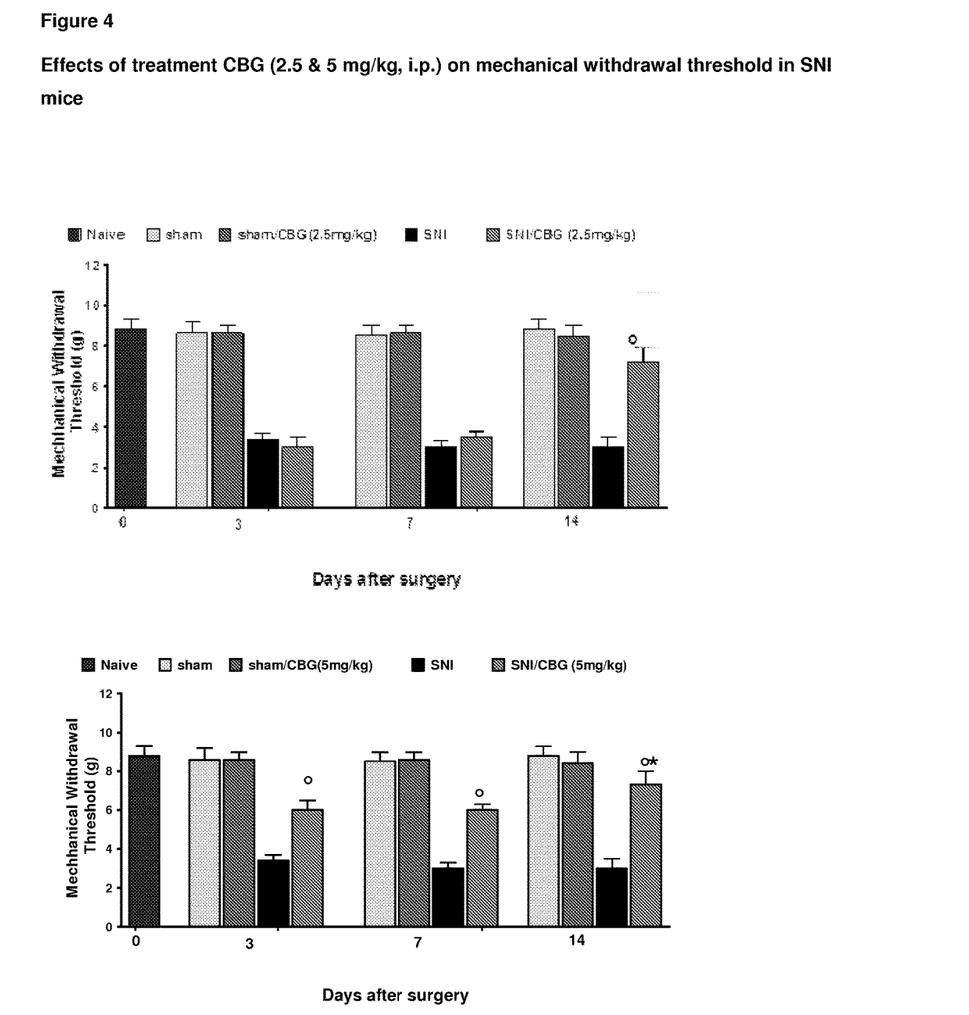
FIG. 4 shows the effects of treatment with CBG (2.5 & 5 mg/kg, i.p.) on mechanical withdrawal threshold in SNI mice.
Figure 5:
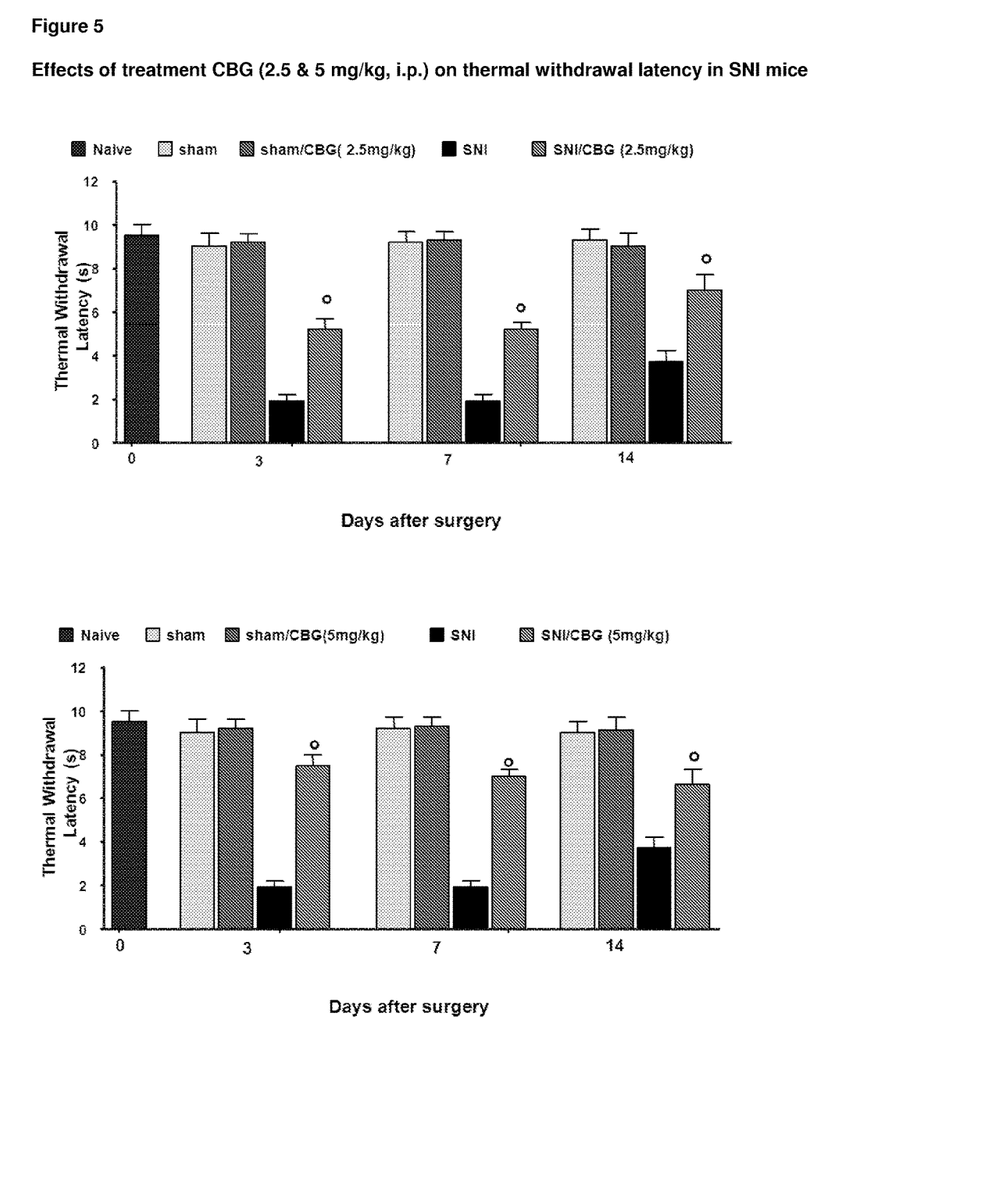
FIG. 5 shows the effects of treatment with CBG (2.5 & 5 mg/kg, i.p.) on thermal withdrawal latency in SNI mice.
Figure 6:
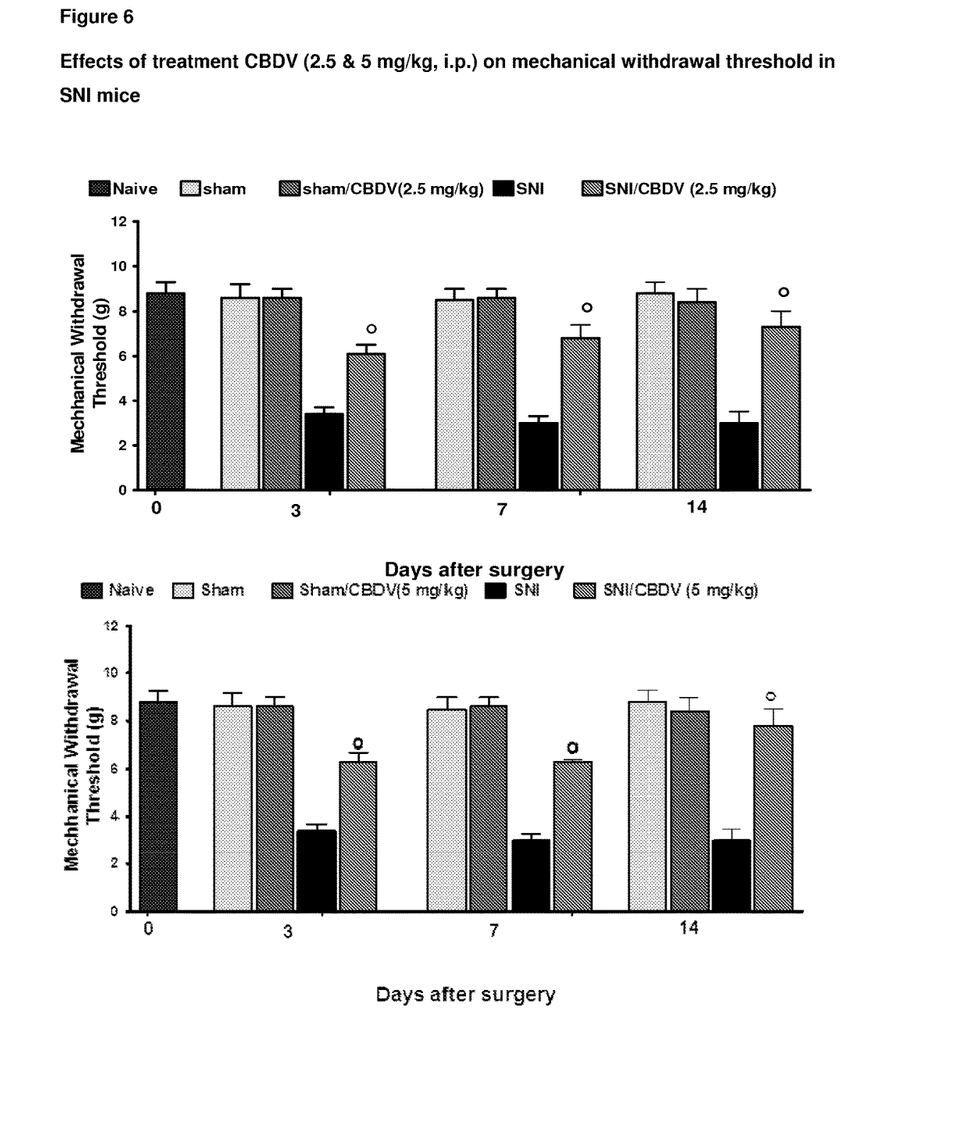
FIG. 6 shows the effects of treatment with CBDV (2.5 & 5 mg/kg, i.p.) on mechanical withdrawal threshold in SNI mice.
Figure 7:
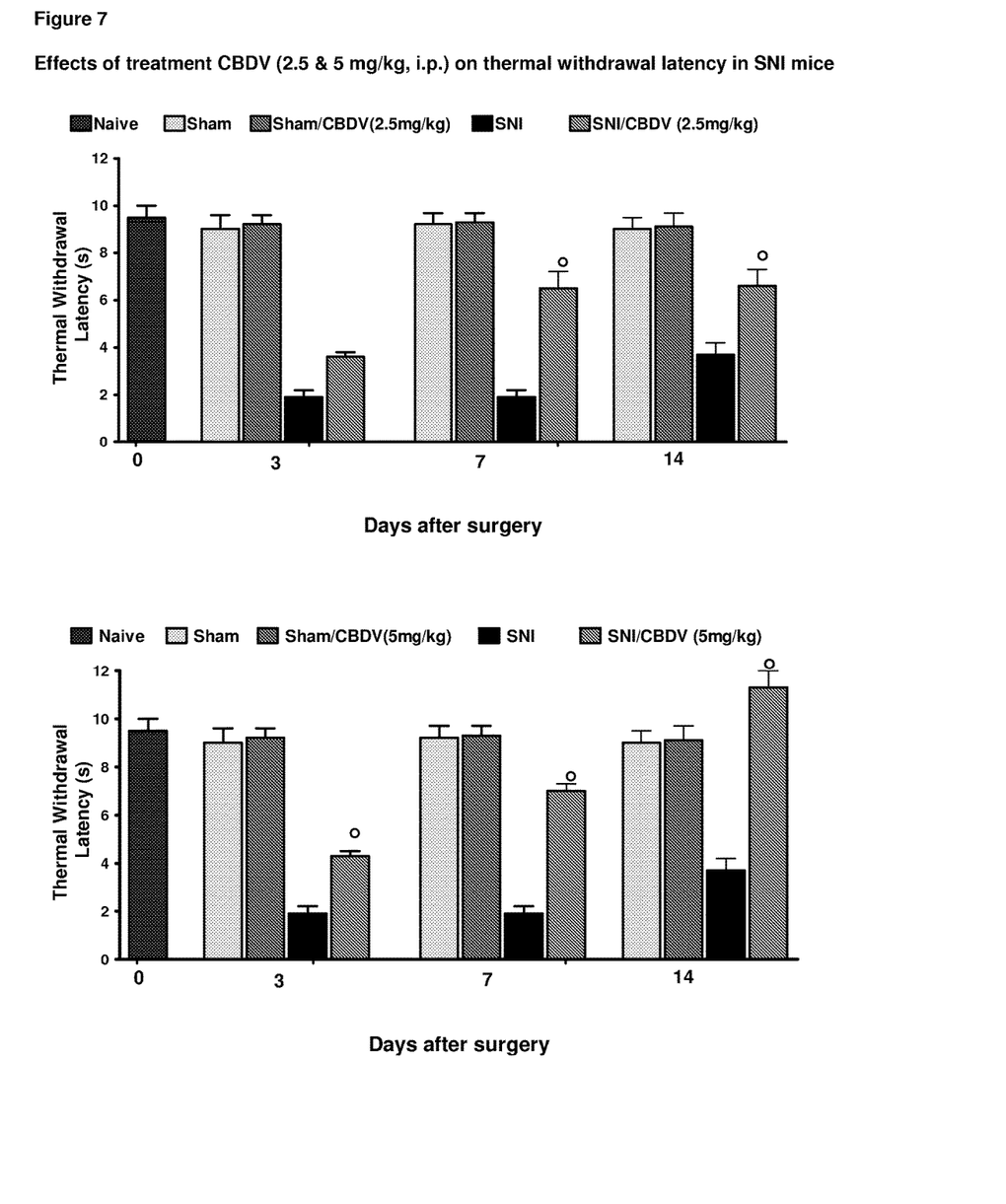
FIG. 7 shows the effects of treatment with CBDV (2.5 & 5 mg/kg, i.p.) on thermal withdrawal latency in SNI mice.
Figure 8:
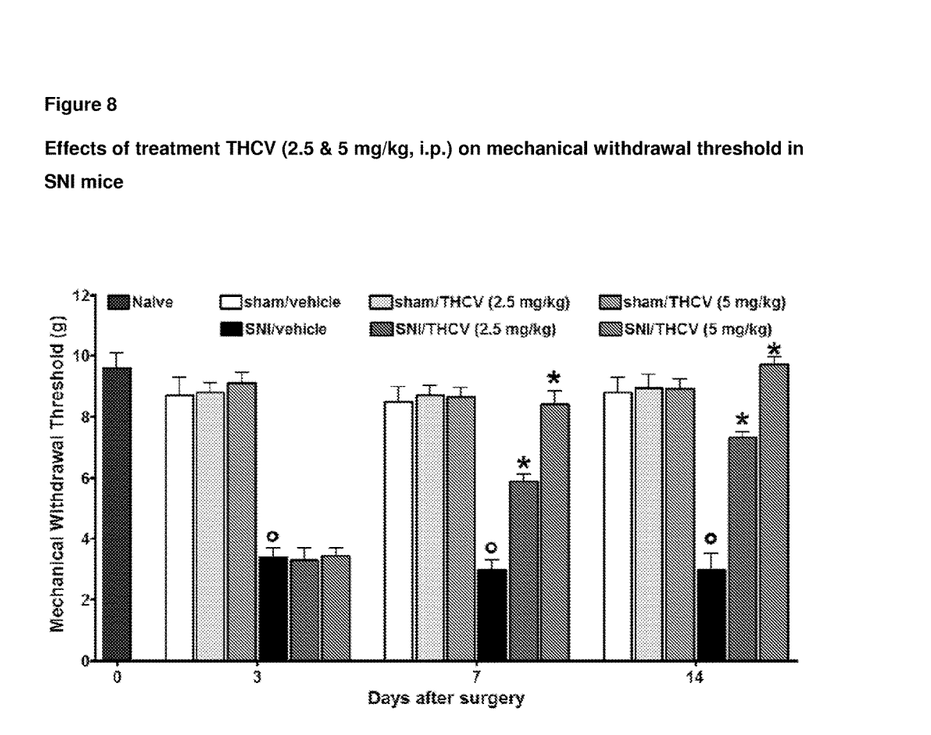
FIG. 8 shows the effects of treatment with THCV (2.5 & 5 mg/kg, i.p.) on mechanical withdrawal threshold in SNI mice.
Figure 9:
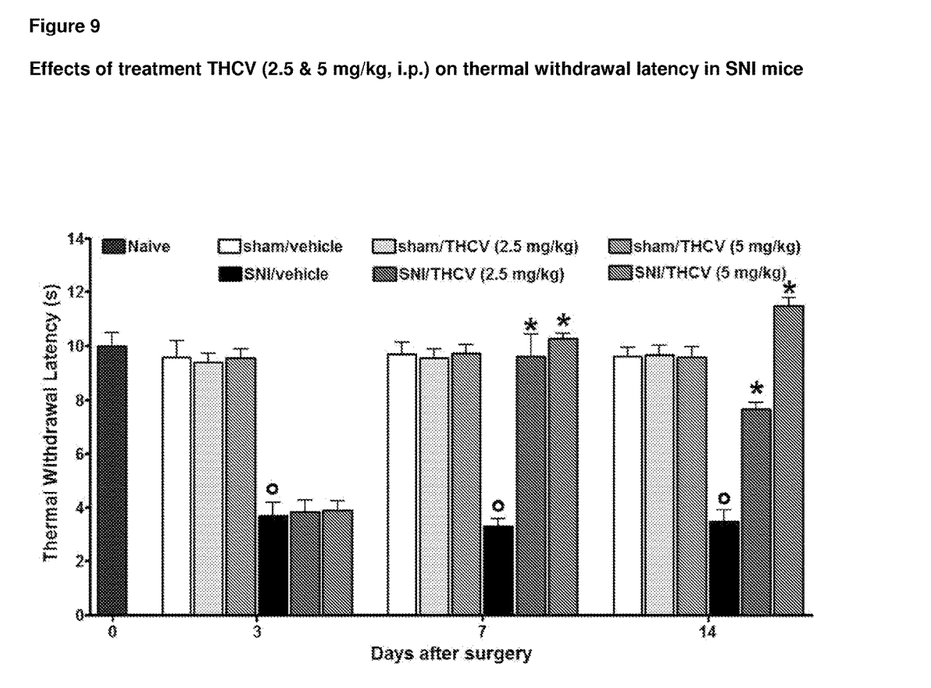
FIG. 9 shows the effects of treatment with THCV (2.5 & 5 mg/kg, i.p.) on thermal withdrawal latency in SNI mice.
Figure 10:
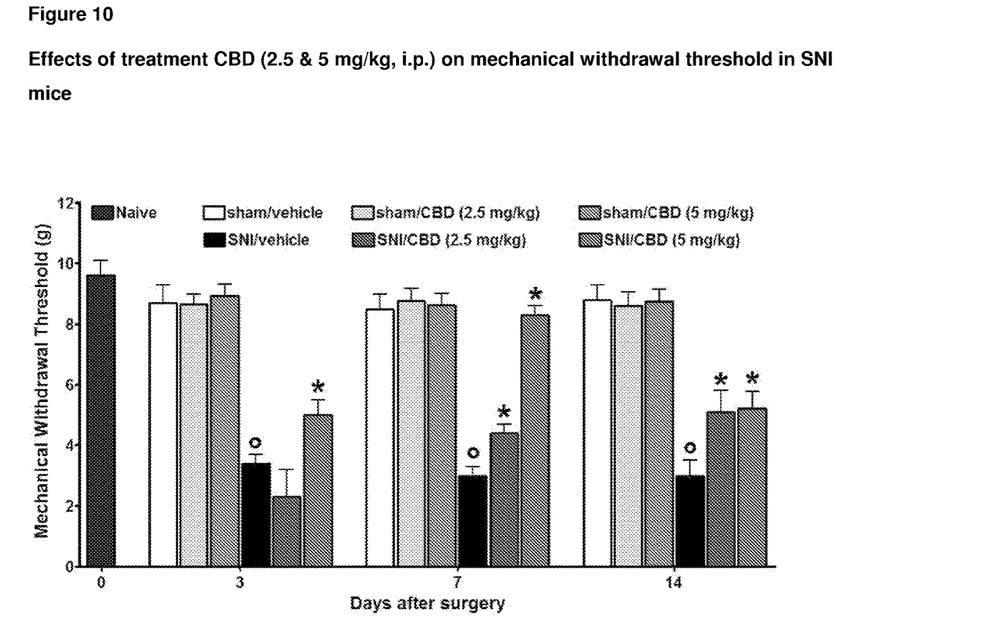
FIG. 10 shows the effects of treatment CBD (2.5 & 5 mg/kg, i.p.) on mechanical withdrawal threshold in SNI mice.
Figure 11:
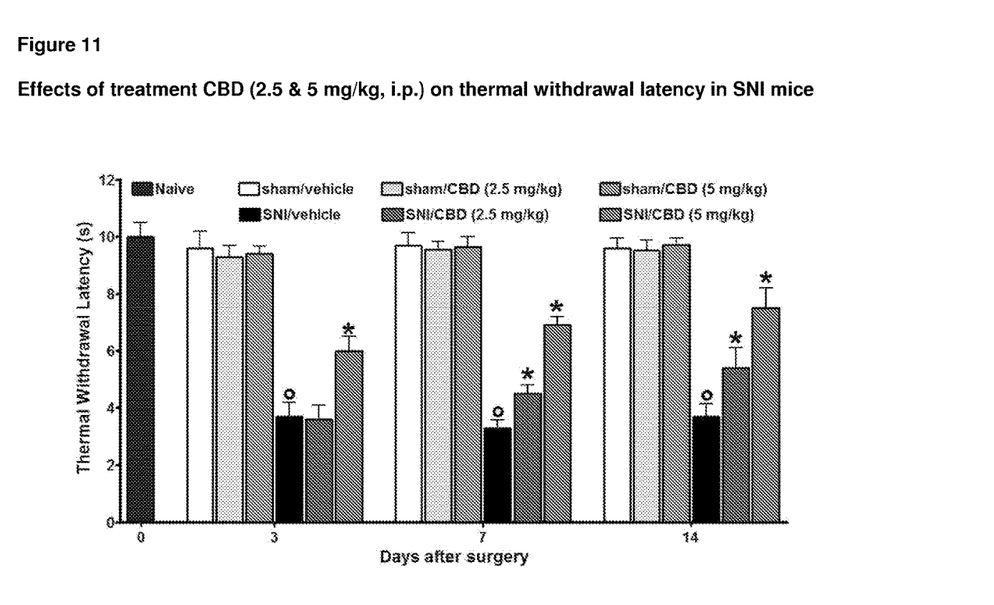
FIG. 11 shows the effects of treatment CBD (2.5 & 5 mg/kg, i.p.) on thermal withdrawal latency in SNI mice.

Pain is one of the most common reasons for a patient to seek medical care and in consequence, pain results in a tremendous number of lost work days per year. There are three general classes of pain: nociceptive pain, neuropathic pain, and psychogenic pain. FIG. 1 illustrates the relationship between different types of pain and conditions affected, such as allodynia and multiple sclerosis.

In nociceptive pain, the stimulation of the sensory nerve endings called nociceptors cause the sensation of pain. Such pain often occurs after injury or surgery. The pain signals are transmitted by the nociceptors to the brain. Often the pain is localised, constant and has an aching or throbbing quality. Once the damage to the tissue heals, the pain usually resolves. Treatment with opioids often resolves nociceptive pain.

Psychogenic pain is a pain disorder that is associated with psychological factors. Some types of mental or emotional problems can cause pain. They can also increase or prolong pain. Headaches, muscle pains, back pain, and stomach pains are some of the most common types of psychogenic pain. People with this pain disorder actually have real pain. The diagnosis is made when all physical causes of pain are ruled out.

Neuropathic pain is the result of an injury or malfunction of the peripheral or the central nervous system. The pain may be triggered by an injury but not necessarily by an injury of the nervous system itself. Neuropathic pain is frequently chronic and is often refractory to treatment with opioids.

Neuropathic pain is caused by abnormalities in the nerves, spinal cord or brain and is a chronic type of non-malignant pain with an estimated prevalence of over 1% of the population. Optimising pain relief in these patients is crucial in helping a patient regain control of his or her life.

The most common cause of neuropathic pain is injury or dysfunction of nerves. Injury or dysfunction of peripheral nerves or nerves descending from the spinal cord results in disinhibition of nerve impulses at the spinal cord which in consequence results in pain. Neuropathic pain can also be centrally mediated, rather than peripheral, in conditions such as spinal cord injury and multiple sclerosis.

Neuropathic pain can therefore be sub-divided into two further classes; peripheral neuropathic pain and central neuropathic pain depending on whether the peripheral or central nervous system is affected.

Patients with peripheral neuropathic pain often experience pain which feels like a burning or electrical pain, whereas others describe their pain as feeling like extreme cold or pins and needles. The pain may be worsened by activity or by wearing clothes over the affected area. The pain may also follow a daily pattern, which may mean it is worse at certain times of the day.

Allodynia is a type of peripheral neuropathic pain. This is a painful response to a typically non-painful stimulus, for example brushing the affected area with a fingertip. The pain tends to increase with repeated stimulation and may spread from the affected area. Allodynic pain can be evoked in response to chemical, thermal (cold or heat) or mechanical low or high intensity stimuli applied either statically or dynamically to skin, joints, bone, muscle or viscera. It is thought that the presence of allodynic pain is a more suitable means of grouping patients suffering from peripheral neuropathic pain than by the specific disease that led to the neuropathic pain.

It is clear that patients who suffer from neuropathic pain can have their quality of life greatly affected by it. The pain can interfere with work and social activities as well as with the amount and quality of sleep that a patient experiences. A successful treatment for the relief of neuropathic pain should improve both the amount of pain that the patient is experiencing as well as improving the patient's quality of life.

The use of pharmaceutical medicaments is the most common treatment for neuropathic pain. Analgesics, antidepressants and anticonvulsants are the drug classes generally in use. The drug carbamezepine, which is an anticonvulsant, is currently the only FDA approved drug which has an indication for neuropathic pain. It has been suggested in post-marketing studies that there is a five- to eight-fold increase in the risk of blood dyscrasias in patients taking carbamezepine. In 7% of patients there has been shown to be a 25% decrease in their white blood cell count.

The use of cannabis as a medicine has long been known and during the $19^{th}$ Century, preparations of cannabis were recommended as a hypnotic sedative which were useful for the treatment of hysteria, delirium, epilepsy, nervous insomnia, migraine, pain and dysmenorrhoea.

Until recent times the administration of cannabis to a patient could only be achieved by preparation of cannabis by decoction which could then be swallowed, or by the patient inhaling the vapours of cannabis by smoking the dried plant material. Recent methods have sought to find new ways to deliver cannabinoids to a patient including those which bypass the stomach and the associated first pass effect of the liver which can remove up to 90% of the active ingested dose and avoid the patient having to inhale unhealthy tars and associated carcinogens into their lungs.

Formulations containing specific, defined ratios of cannabinoids may be formulated from pure, synthetic or isolated cannabinoids or from extracts derived from the cannabis plant in combination with pharmaceutical carriers and excipients.

Cannabinoids are a group of chemicals known to activate cannabinoid receptors in cells. Phytocannabinoids are the cannabinoids derived from cannabis plants. Endocannabinoids are endogenous cannabinoids found in humans and other animals. The phytocannabinoids can be isolated from plants or produced synthetically. When isolating the phytocannabinoids from plants they can be purified to the extent that all of the other naturally occurring compounds, such as, other minor cannabinoids and plant molecules such as terpenes are removed. This purification results in a purity of greater than 99% (w/w) of the target cannabinoid.

It has been shown previously that the cannabinoid cannabidiol (CBD) administered as a purified compound can partially relieve neuropathic pain (Costa et al., 2004). This was shown using the neuropathic pain model of chronic constriction injury of the rat sciatic nerve and testing the effectiveness of the test article with thermal and mechanical hyperalgesia and mechanical allodynia. These animal models are used to predict the effectiveness of a test compound on neuropathic pain.

More recently the applicant has shown in their granted UK patent, GB2439393, that a plant extract comprising a defined ratio of CBD to THC is more effective at treating peripheral neuropathic pain than the purified components alone. The ratio of CBD to THC which is effective is between 20:1 to 28:1.

The patent application PCT/GB2006/004063 describes the use of an extract of cannabis wherein the THC to CBD ratio is about 1:1. The extract was found to be beneficial in the treatment of peripheral neuropathic pain that is characterised by post-herpetic neuralgia.

Neuropathic pain is often associated with a diverse and complex set of pain stimuli and as such is difficult to treat effectively as the response to treatment is unpredictable.

Surprisingly, the applicants have found that administration of the cannabinoids cannabigerol (CBG), cannabichromene (CBC), cannabidivarin (CBDV) and tetrahydrocannabivarin (THCV) are effective in the treatment of an animal model of neuropathic pain. Since neuropathic pain appears to be refractory to conventional analgesic treatment, such as opiates and non-steroidal anti-inflammatory drugs, the animal studies described herein represents an important finding for clinical settings.

BRIEF SUMMARY OF THE DISCLOSURE

In accordance with a first aspect of the present invention there is provided one or more of the phytocannabinoids: cannabichromene (CBC), cannabigerol (CBG), cannabidivarin (CBDV) and/or tetrahydrocannabivarin (THCV), for use in the treatment of neuropathic pain.

In accordance with a second aspect of the present invention there is provided the use of one or more of the phytocannabinoids: cannabichromene (CBC), cannabigerol (CBG), cannabidivarin (CBDV) and/or tetrahydrocannabivarin (THCV), in the manufacture of a medicament for use in the treatment of neuropathic pain.

In accordance with a third aspect of the present invention there is provided a method of treating a patient with neuropathic pain comprising administering an effective amount of one or more phytocannabinoids taken from the group: cannabichromene (CBC), cannabigerol (CBG), cannabidivarin (CBDV) and/or tetrahydrocannabivarin (THCV).

These cannabinoids may also be used in combination THC and/or CBD.

Preferably the neuropathic pain is peripheral neuropathic pain, more preferably the peripheral neuropathic pain is allodynia.

Preferably the cannabinoids are present in a dose effective to relieve neuropathic pain.

A low dose of cannabinoids is defined as an effective human daily dose of cannabinoids of below 10 mg and a high dose of cannabinoids is defined as an effective human daily dose of cannabinoids of 50 mg or above. An intermediate dose is defined as being between 10 mg and 50 mg.

Preferably the effective human daily dose of cannabinoids is between 5 mg and 100 mg. More preferably the effective human daily dose of cannabinoids is between 10 mg and 50 mg. More preferably still the effective human daily dose of cannabinoids is between 12 mg and 24 mg.

Preferably the cannabinoids are packaged for use for an extended treatment period. An extended period will be more preferable, more preferably more than 3 days, more preferably still the extended treatment period is at least 7 days.

In a further embodiment of the present invention the one or more of phytocannabinoids are used in combination with one or more other currently approved medicinal substances used in the treatment of neuropathic pain. These medicinal substances include for example analgesics, antidepressants, and anticonvulsants.

BRIEF DESCRIPTION OF THE DRAWINGS

Embodiments of the invention are further described hereinafter with reference to the accompanying drawings, in which:

FIGS. 10 and 11 are included as comparative data given that the use of CBD in neuropathic pain is known.

DETAILED DESCRIPTION

Peripheral neuropathic pain is produced by multiple etiological factors that initiate a number of diverse mechanisms at different sites and in different disease states. Spared nerve injury (SNI) consists of partial ligation and transaction of the sciatic nerve which evolves in neuropathic pain whose typical manifestations are represented by thermal hyperalgesia and tactile allodynia.

Chronic pain symptoms are measured through changes in thermoceptive responses (which is indicative of thermal hyperalgesia) using Plantar Test Apparatus (Ugo Basile, Varese, Italy) and in mechanical paw withdrawal threshold (which is indicative of mechanical allodynia) by a Dynamic Plantar Aesthesiometer (Ugo Basile, Varese, Italy). Nociceptive responses were measured before and after surgery in groups of mice differently treated (vehicle or drugs different combinations).

The Example below details the results obtained using four different cannabinoids which have not previously been demonstrated as having the ability to reduce neuropathic pain, namely: CBG, CBC, CBDV, and THCV. The cannabinoids were compared to the cannabinoid CBD which has previously been demonstrated to be useful in the treatment of neuropathic pain.

Example 1: The Effects of Cannabinoids in Two Animal Models of Neuropathic Pain Materials and Methods The cannabinoids tested were CBG, CBC, CBDV, and THCV. In addition the cannabinoid CBD was used as this cannabinoid has previously demonstrated positive results in the animal models of neuropathic pain used in this example. The cannabinoids were prepared from whole plant extracts of cannabis plants which had been purified. The cannabinoids were dissolved in ringer/0.5% dimethyl sulfoxide (DMSO), for intraperitoneal (i.p.) administration.

Male CD-1 mice (35-40 g) were housed, 3 per cage, under controlled illumination (12:12 h light:dark cycle; light on 06.00 h) and environmental conditions (room temperature 20-22° C., humidity 55-60%) for at least 1 week before the commencement of experiments. Mouse chow and tap water were available ad libitum. The experimental procedures were approved by the Ethic Committee of the Second University of Naples. Animal care was in compliance with the IASP and European Community (E.C. L358/1 18/12/86) guidelines on the use and protection of animals in experimental research. All efforts were made to minimize animal suffering and to reduce the number of animals used.

Behavioural testing was performed before surgery to establish a baseline for comparison with post-surgical values. Mononeuropathy was induced according to the method of Bourquin and Decosterd (2006).

Mice were anaesthetized with sodium pentobarbital (60 mg/kg i.p.). The right hindlimb was immobilized in a lateral position and slightly elevated. Incision was made at mid-thigh level using the femur as a landmark. The sciatic nerve was exposed at mid-thigh level distal to the trifurcation and freed of connective tissue; the three peripheral branches (sural, common peroneal, and tibial nerves) of the sciatic nerve were exposed without stretching nerve structures.

Both tibial and common peroneal nerves were ligated and transacted together. A micro-surgical forceps with curved tips was delicately placed below the tibial and common peroneal nerves to slide the thread (5.0 silk, Ethicon, Johnson, and Johnson Intl, Brussels, Belgium) around the nerves. A tight ligation of both nerves was performed. The sural nerve was carefully preserved by avoiding any nerve stretch or nerve contact with surgical tools. Muscle and skin were closed in two distinct layers with silk 5.0 sutures.

Intense, reproducible and long-lasting thermal hyperalgesia and mechanical allodynia-like behaviors are measurable in the non-injured sural nerve skin territory. The SNI model offers the advantage of a distinct anatomical distribution with an absence of co-mingling of injured and non-injured nerve fibers distal to the lesion such as the injured and non-injured nerves and territories can be readily identified and manipulated for further analysis (i.e. behavioral assessment).

The sham procedure consisted of the same surgery without ligation and transection of the nerves.

The groups of mice were divided as follows, each cannabinoid tested has its own group of mice:
i) Naïve control mice (n=8);
ii) Sham-operated mice treated with vehicle (n=8);
iii) Sham-operated mice treated with cannabinoid (n=8);
iv) SNI mice treated with vehicle (n=8);
v) SNI mice treated with cannabinoid (n=8).

The cannabinoids were dosed daily for 14 days. Doses for all cannabinoids tested were: 2.5 and 5.0 mg/Kg. Vehicle solution was 0.5% DMSO in ringer solution.

Nociceptive Behaviour

Mechanical allodynia was measured by using Dynamic Plantar Anesthesiometer (Ugo Basile, Varese, Italy). Mice were allowed to move freely in one of the two compartments of the enclosure positioned on the metal mesh surface. Mice were adapted to the testing environment before any measurements were taken. After that, the mechanical stimulus was delivered to the plantar surface of the hindpaw of the mouse from below the floor of the test chamber by an automated testing device. A steel rod (2 mm) was pushed with electronical ascending force (0-30 g in 10 sec). When the animal withdrew its hindpaw, the mechanical stimulus was automatically withdrawn and the force recorded to the nearest 0.1 g.

Thermal hyperalgesia was evaluated by using a Plantar Test Apparatus (Ugo Basile, Varese, Italy). On the day of the experiment each animal was placed in a plastic cage (22 cm×17 cm×14 cm; length×width×height) with a glass floor. After a 60 min habituation period, the plantar surface of the hind paw was exposed to a beam of radiant heat through the glass floor. The radiant heat source consisted of an infrared bulb (Osram halogen-bellaphot bulb; 8 V, 50 W). A photoelectric cell detected light reflected from the paw and turned off the lamp when paw movement interrupted the reflected light. The paw withdrawal latency was automatically displayed to the nearest 0.1 sec; the cut-off time was 20 sec in order to prevent tissue damage.

Nociceptive responses for thermal and mechanical sensitivity were expressed as thermal paw withdrawal latency (PWL) in seconds and mechanical paw withdrawal threshold (PWT) in grams.

Each mouse served as its own control, the responses being measured both before and after surgical procedures. PWL and PWT were quantified by an observer blinded to the treatment.

Statistical Analysis

Behavioural and molecular data were shown as means±S.E.M. ANOVA, followed by Student-Neuman-Keuls post hoc test, was used to determine the statistical significance among groups. $P<0.01$ was considered statistically significant.

Results

Mechanical Withdrawal Threshold

FIGS. 2, 4, 6, 8 and 10 demonstrate the mechanical withdrawal threshold data obtained for the cannabinoids tested (CBC, CBG, CBDV, THCV and CBD (comparator) respectively). The bar charts illustrate the amount of weight in grams required to make the animal withdraw its hindpaw. As can be seen all of the cannabinoids tested were able allow the animals with the SNI to increase the amount of weight applied before it withdrew its paw, and as such were able to prevent, at varying degrees, mechanical allodynia at 3, 7 and 14 days after spared nerve injury. The analgesic effects were dose-dependent as greater effects were observed in animals receiving the 5.0 mg/kg dose of cannabinoid.

Thermal Withdrawal Latency

FIGS. 3, 5, 7, 9 and 11 demonstrate the thermal withdrawal latency data obtained for the cannabinoids tested (CBC, CBG, CBDV, THCV and CBD (comparator) respectively). The bar charts illustrate the amount of time in seconds before the animal withdrew its paw from the heat source. As can be seen all of the cannabinoids tested were able to allow the animals with the SNI to increase the amount of time before it withdrew its paw, and as such were able to prevent, at varying degree, thermal hyperalgesia at 3, 7 and 14 days after spared nerve injury.

For the cannabinoids CBC, CBG, THCV and CBD the effects do not appear to be dose-dependent as animals treated with 2.5 and 5 mg/kg had similar withdrawal latencies, or are reaching maximum effect at a lower dose However for the cannabinoid CBDV dose-dependent effects were observed. Animals treated with the 2.5 mg/kg dose had similar withdrawal latencies to the control group at day 3 post nerve injury. However, animals treated with the 5.0 mg/kg dose were able to increase the amount of time before the paw was withdrawn from the heat source, to the extent that at 14 days post nerve injury, with this group had similar withdrawal latencies to the naive and sham control animals.

Combination of Data

In order to ascertain the different degrees of effectiveness of the cannabinoids tested the tables below describe the data generated in this example in tabular form.

Table 1 below describes the effects of the treatment with cannabinoids on mechanical withdrawal threshold in mice.

TABLE 1

Mechanical withdrawal threshold - combined data

| TEST ARTICLE | MECHANICAL WITHDRAWAL THRESHOLD (g) | | |
|---|---|---|---|
| | DAY 3 | DAY 7 | DAY 14 |
| Naive | 9.5 | 9.5 | 9.5 |
| Sham/vehicle | 8.8 | 8.6 | 9.0 |
| SNI/vehicle | 3.2 | 3.0 | 3.1 |
| SNI/CBC (2.5 mg/kg) | 2.4 | 4.5 | 5.0 |
| SNI/CBG (2.5 mg/kg) | 3.4 | 6.1 | 7.8 |
| SNI/CBDV (2.5 mg/kg) | 6.8 | 7.0 | 7.8 |
| SNI/THCV (2.5 mg/kg) | 3.0 | 6.2 | 7.5 |
| SNI/CBD (2.5 mg/kg) | 2.2 | 4.8 | 5.2 |
| SNI/CBC (5 mg/kg) | 5.1 | 9.7 | 5.2 |
| SNI/CBG (5 mg/kg) | 6.0 | 6.1 | 7.8 |
| SNI/CBDV (5 mg/kg) | 6.7 | 6.6 | 7.7 |
| SNI/THCV (5 mg/kg) | 3.2 | 8.5 | 9.8 |
| SNI/CBD (5 mg/kg) | 5.0 | 8.6 | 5.3 |

As can be seen from Table 1 above most of the cannabinoids at the 2.5 mg/kg dose show a slight increase in the amount of weight applied before the animal withdraws its paw, this effect appears to increase over time from day 3 to day 7 to day 14. With the 2.5 mg/kg dose of the cannabinoid CBDV there is however a dramatic increase in the mechanical withdrawal latency even at the day 3 time point inferring that this cannabinoid is able to be effective quickly, whereas the other cannabinoids take a week or more to become effective.

At the 5.0 mg/kg dose all of the cannabinoids except THCV were able to increase the amount of weight applied before the animal withdrew its paw. The cannabinoids CBC and CBD showed a large increase at day 7; however this latency decreased again at the 14 day time point.

Surprisingly these data demonstrate that at both of the doses tested the cannabinoid CBDV was shown to have the highest mechanical withdrawal latency of all the cannabinoids. The cannabinoids CBG and THCV also showed good efficacy as they had reasonably high mechanical withdrawal latencies. However the cannabinoids CBC and CBD were shown to be relatively ineffective in the treatment of neuropathic pain at this dose. This finding demonstrates that the cannabinoids CBDV, THCV and CBG are superior to CBD in their ability to treat the neuropathic pain brought about by the animal model used in this experiment.

Table 2 below describes the effects of the treatment with cannabinoids on thermal withdrawal latency in mice.

TABLE 2

Thermal withdrawal latency - combined data

| TEST ARTICLE | THERMAL WITHDRAWAL LATENCY (s) | | |
|---|---|---|---|
| | DAY 3 | DAY 7 | DAY 14 |
| Naive | 10.0 | 10.0 | 10.0 |
| Sham/vehicle | 9.7 | 9.7 | 9.7 |
| SNI/vehicle | 3.8 | 3.5 | 3.9 |
| SNI/CBC (2.5 mg/kg) | 3.7 | 4.8 | 5.2 |
| SNI/CBG (2.5 mg/kg) | 5.5 | 5.4 | 7.0 |
| SNI/CBDV (2.5 mg/kg) | 3.8 | 6.4 | 6.5 |
| SNI/THCV (2.5 mg/kg) | 3.8 | 9.8 | 7.6 |
| SNI/CBD (2.5 mg/kg) | 3.5 | 4.2 | 5.6 |
| SNI/CBC (5 mg/kg) | 6.0 | 7.0 | 7.2 |
| SNI/CBG (5 mg/kg) | 7.8 | 7.6 | 7.5 |
| SNI/CBDV (5 mg/kg) | 4.0 | 7.2 | 11.0 |
| SNI/THCV (5 mg/kg) | 3.9 | 10.5 | 11.9 |
| SNI/CBD (5 mg/kg) | 5.8 | 7.0 | 7.5 |

As can be seen from Table 2 most of the cannabinoids at the 2.5 mg/kg dose shows a slight increase in the amount of time before the animal withdraws its paw this effect appears to increase over time from day 3 to day 7 to day 14. At the day 3 time point only the 2.5 mg/kg dose CBG appears to have any increase in the amount of thermal withdrawal latency. For the cannabinoid THCV there appears to be a large increase at the day 7 time point which then decreases after a further 7 days.

At the 5.0 mg/kg dose the cannabinoids CBC, CBG and CBD were able to increase the amount of time before the animal withdrew its paw at the three day time point. After a week of treatment with the cannabinoids however all test groups showed an increase in the thermal withdrawal latency. THCV and CBDV both showed a large increase after 14 days of treatment inferring that the effectiveness of the cannabinoids builds up over time.

Surprisingly these data demonstrate that at the 2.5 mg/kg dose the cannabinoid CBG was shown to have the highest thermal withdrawal latency of all the cannabinoids. The cannabinoids CBDV and THCV also showed good efficacy as they had reasonably high mechanical withdrawal latencies. However the cannabinoids CBC and CBD were shown to be relatively ineffective in the treatment of neuropathic pain at this dose. At the 5.0 mg/kg dose both the cannabinoids CBDV and THCV were shown to be most effective. This finding demonstrates that the cannabinoids CBDV, THCV and CBG are superior to CBD in their ability to treat the neuropathic pain brought about by the animal model used in this experiment.

The human dose equivalent (HED) can be estimated using the following formula:

$$HED = \text{Animal dose}(mg/kg) \text{ multiplied by Animal } \frac{K_m}{\text{Human } K_m}$$

The $K_m$ for a mouse is 3 and for a rat the value is 6 and the $K_m$ for a human is 37.

Thus, for a human of approximately 60 kg a 2.5 mg/kg dose in a mouse would equate to a human daily dose of about 12 mg.

The invention claimed is:

1. A method of treating a patient with neuropathic pain consisting essentially of administering to the patient an effective amount of cannabidivarin (CBDV) wherein the CBDV is of a purity of greater than 99% (w/w), or is produced synthetically and does not include cannabidiol (CBD) and/or tetrahydrocannabinol (THC).

2. The method as claimed in claim 1, wherein the neuropathic pain is peripheral neuropathic pain.

3. The method as claimed in claim 2, wherein the peripheral neuropathic pain is allodynia.

4. The method as claimed in claim 1, wherein the CBDV is present in an effective human daily dose to relieve neuropathic pain.

5. The method as claimed in claim 4, wherein the effective human daily dose of CBDV is between 5 mg and 100 mg.

6. The method as claimed in claim 5, wherein the effective human daily dose of CBDV is between 10 mg and 50 mg.

7. The method as claimed in claim 1, wherein the CBDV is packaged for use for an extended treatment period.

8. The method as claimed in claim 7, wherein the extended treatment period is at least 7 days.

9. The method as claimed in claim 1, wherein the CBDV is administered to the patient in combination with one or more other medicinal substances used in the treatment of neuropathic pain.

* * * * *